(12) United States Patent
Lamb (10) Patent No.: US 8,784,396 B2
(45) Date of Patent: Jul. 22, 2014

(54) TAMPON

(76) Inventor: Peter James Brian Lamb, Centurion (ZA)

( * ) Notice: Subject to any disclaimer, the term of this patent is extended or adjusted under 35 U.S.C. 154(b) by 1002 days.

(21) Appl. No.: 10/484,146

(22) PCT Filed: Jul. 19, 2002

(86) PCT No.: PCT/IB02/02815
§ 371 (c)(1),
(2), (4) Date: Jan. 16, 2004

(87) PCT Pub. No.: WO03/007862
PCT Pub. Date: Jan. 30, 2003

(65) Prior Publication Data
US 2004/0199137 A1 Oct. 7, 2004

(30) Foreign Application Priority Data

Jul. 19, 2001 (ZA) .................................. 2001/5966
Sep. 13, 2001 (ZA) .................................. 2001/7563

(51) Int. Cl.
*A61F 13/15* (2006.01)
*A61F 13/20* (2006.01)

(52) U.S. Cl.
USPC ................. 604/385.17; 604/385.18; 604/904

(58) Field of Classification Search
USPC ................................. 604/385.17, 904, 385.18
See application file for complete search history.

(56) References Cited

U.S. PATENT DOCUMENTS

| | | | | |
|---|---|---|---|---|
| 2,340,311 A * | 2/1944 | Donovan | ...................... | 604/363 |
| 2,771,882 A * | 11/1956 | Leupold | ................... | 604/385.17 |
| 3,428,044 A | 2/1969 | Withead et al. | | |
| 3,595,236 A | 7/1971 | Corrigan et al. | | |
| 3,976,075 A | 8/1976 | Chinai et al. | | |
| 4,507,413 A * | 3/1985 | Thoma et al. | ................... | 524/42 |
| 4,610,659 A * | 9/1986 | Friese | .............. | 604/11 |
| 4,952,211 A * | 8/1990 | Snider | .......... | 604/285 |
| 5,403,300 A | 4/1995 | Howarth | | |
| 5,542,914 A * | 8/1996 | Van Iten | .......... | 604/11 |
| 5,817,077 A * | 10/1998 | Foley et al. | .......... | 604/363 |
| 6,086,909 A * | 7/2000 | Harrison et al. | .............. | 424/430 |
| 6,860,874 B2 * | 3/2005 | Gubernick et al. | ...... | 604/385.18 |
| 7,722,588 B1 * | 5/2010 | Johnson et al. | .......... | 604/385.18 |
| 8,216,202 B2 * | 7/2012 | Minoguchi et al. | ...... | 604/385.17 |
| 2002/0143305 A1* | 10/2002 | Yang et al. | ..................... | 604/363 |
| 2005/0249774 A1* | 11/2005 | Pauletti et al. | ................ | 424/423 |
| 2005/0256486 A1* | 11/2005 | Carasso et al. | ........... | 604/385.18 |
| 2010/0130951 A1* | 5/2010 | Pierson et al. | ................ | 604/358 |

* cited by examiner

*Primary Examiner* — Michele M Kidwell
(74) *Attorney, Agent, or Firm* — James Ray & Assoc (57) ABSTRACT

This invention relates to a tampon (10). The tampon includes an elongate absorbent body (12) and at least one surface formation (34, 36, 38, 40) applied over an exterior surface of the absorbent body. The at least one surface formation is of a material different to the absorbent body and is configured to inhibit expansion of at least a portion of the absorbent body i-n use due to absorption of menses by the absorbent body, and/or to facilitate insertion and seating of the tampon in a vagina. The invention extends to a tampon which includes an elongate absorbent body which is non-circular in outline in end view. The invention further extends to a tampon which has a particular correct angular orientation relative to its longitudinal axis, with which it is to be inserted into a vagina, the correct angular orientation being clearly visible to a user.

20 Claims, 5 Drawing Sheets

TAMPON

THIS INVENTION relates to a tampon.

Catamenial tampons are widely used and there is a long felt need to improve their efficiency in preventing leakage of menses or menstrual fluid and the level of comfort with which they can be worn, and also to reduce the occurrence of negative side-effects caused by their use.

In accordance with a first aspect of the invention, there is provided a tampon which includes an elongate absorbent body and at least one surface formation, of a material different to the absorbent body, applied over an exterior surface of the absorbent body, the surface formation being configured to inhibit expansion of at least a portion of the absorbent body in use due to absorption of menses by the absorbent body, and/or to facilitate insertion and seating of the tampon in a vagina.

When configured to inhibit expansion, the or each surface formation thus ensures that the portion of the absorbent body affected thereby retains its shape and dimensions to at least some extent, whilst other portions of the body not affected thereby expand relatively freely during absorption of menses.

The absorbent body may have a shape and dimensions as described hereinafter for the tampon of a second aspect of the invention.

The or at least one of the surface formations, or a portion of the or at least one of the surface formations may be in the form of a coating on a portion of the exterior surface of the absorbent body.

The or each surface formation may be of a synthetic plastics material or of a polymeric material. The material may be an elastic material.

The or each surface formation may be of a material with no or significantly reduced water absorbent properties compared to a material of the absorbent body, e.g. cellulose. The coating may consist of any thermoplastic, elastomeric or resin type material. These polymeric materials can be applied onto the surface of the tampon by conventional techniques, e.g. dipping, spray coating, low pressure injection moulding, jet coating printing and one or two reactive component injection moulding.

The choice of the adequate application technique depends on the nature of the polymeric material. Emulsions and/or dispersions are preferentially applied by dipping, spraying or jet coating processes. Low pressure injection moulding processes can be considered for reactive or non reactive bulk materials having sufficiently low viscosities at temperatures which do not damage the cellulose or other base material of the tampon. For reactive one or two component systems known mixing and injection devices can be used.

It has already been mentioned that the polymeric materials of this invention possess no or a significantly reduced water absorbence. This property can be described by the equilibrium contact angle of water on corresponding smooth polymer surfaces. Contact angles between 20° and 120°, preferentially 30° and 120°, specifically 40° and 110°, more specifically 60° and 110° are beneficial. This contact angle difference of at least 20° compared to a cellulosic base material (complete wetting) guarantees that blood and other body liquids are directed to specifically designed portions of the tampon away from the surface formations.

Preferred thermoplastic materials comprise homo- and copolymers based on acrylic/methacrylic acid, polyesters, polyamides, polyhaloolefines and polyolefines. Preferred elastomeric materials comprise homo- and copolymers based on butadiene, isoprene and isobutene. Depending on the composition reactive systems can belong to the thermoplastic, elastomeric or resin type of material. Polyurea- and/or polyurethane structures comprising homo- and/or copolymers are preferred. It is within the scope of the invention to modify the thermoplastic, elastomeric and reactive system based polymers by addition of adequate cross-linking agents.

A leading end or nose portion of the absorbent body may include a surface formation in the form of a coating. This renders the tampon easier and less painful to insert and allows the leading end easily to slip into the posterior vaginal fornix and allows the tampon to be located higher up in the vagina, thereby making use of extra space provided by the posterior vaginal fornix. In use, the cervix can thus trap the tampon of the invention, which is higher up in the vagina than is the case of conventional tampons, thereby reducing the risk that the tampon will slip down the vagina and wedge between the levator ani, which can be very painful to a user of a tampon.

An exterior surface portion of the tampon which in use will be in contact with the cervix of a user may include a surface formation in the form of a coating. The delicate lining of the cervical canal of some women is exposed at the opening of the cervix, particularly in women who gave natural birth to children (cervical ectropion or erosion). Conventional tampons may cause microscopic trauma to the delicate lining of a cervical erosion or ectropion which may aggravate cervical infection, discharge and bleeding. The coated tampon of the invention may reduce cervicitis and bleeding. Decreasing mucosal microtrauma has advantages in combating HIV/aids transmission, as will be appreciated. Furthermore, as the portions of the absorbent body affected by surface formations configured to inhibit expansion, and in particular the leading end, do not in use expand or swell to the same extent as a conventional tampon, the risk of plugging of the cervix and the resultant haematometra and retrograde menstruation with concomitant symptomatology is reduced.

A trailing end or tail portion of the absorbent body may include a surface formation configured to inhibit expansion of the trailing end or tail portion of the absorbent body. The surface formation may be in the form of a coating defining an end cap for the trailing end or tail portion of the absorbent body. Advantageously, such an end cap inhibits discharge of menses from the rear end of the absorbent body caused by squeezing of the absorbent body during movement of the body of a user. The end cap ensures that the rear end of the absorbent body in use retains its shape and dimensions at least to some extent and inhibits the formation of a tapered or pointed rear end due to swelling. This reduces the risk that the absorbent body will wedge between the levator ani.

At least one surface formation, or a portion of at least one surface formation may be in the form of a thin band or strip applied to the exterior surface of the absorbent body. In one embodiment of the invention, a plurality of bands or strips may be provided on the exterior surface of the absorbent body. At least some of the bands or strips may be in the form of broken or discontinuous lines.

Some of the bands or strips may longitudinally extend over the exterior surface of the absorbent body and may be transversely spaced from each other. The longitudinally extending bands or strips may be parallel to each other. Although discontinuous longitudinally extending spaced bands or strips will still allow expansion of the absorbent body, insertion and wear of the tampon will be easier and more comfortable and less microtrauma will be caused to the vaginal mucosa of a user.

Some of the bands or strips may transversely extend over the exterior surface of the absorbent body and may be longitudinally spaced from each other.

The surface formation or surface formations may stand proud of the exterior surface of the absorbent body thereby to form or define a raised pattern on the exterior surface of the absorbent body. The raised pattern can advantageously assist in inhibiting slipping of the tampon in use towards the vaginal opening, by interacting with the rugae of the vagina.

In accordance with a second aspect of the invention, there is provided a tampon which includes an elongate absorbent body which is non-circular in outline in end view.

The body may have extremities which fall on the outline of an oval or ellipse in end view to provide the body with a width which is greater than a thickness thereof. Typically, the body has a length which is greater than its width.

The body may define an upper or superior surface, a lower or posterior surface, and two opposed side edges which extend longitudinally.

At least one of the upper surface and the lower surface may be non-planar.

At least a portion, e.g. a longitudinally extending central portion, of the upper surface may be concave when the body is viewed in cross-section. The concave portion of the upper surface advantageously conforms in use with the anterior wall of the vagina, which is convex as a result of pressure from the bladder (when viewed in cross section).

At least a portion, e.g. a longitudinally extending central portion, of the lower surface may be concave when the body is viewed in cross-section. The concave portion of the lower surface advantageously conforms in use with the posterior wall of the vagina, which is convex as a result of pressure from the rectum (when viewed in cross section).

The upper surface of the body may converge or drop down towards the lower surface of the body to end in a rounded leading end or nose when the body is viewed in side view.

Corners of the body may be rounded when the body is viewed in plan view.

In one embodiment of the invention, the body is generally rectangular in plan view. The body may also be generally rectangular in side view.

In another embodiment of the invention, the body is thickened in a trailing end or tail portion thereof relative to a leading end or nose portion thereof when the body is viewed in side view. A transitional region between the trailing end or tail portion and the leading end or nose portion may be concavely curved. Such a concavely curved transitional region advantageously accommodates in use the portio vaginalis of the cervix uteri, with the front portion of the body fitting into the posterior vaginal fornix. The thickened trailing end or tail portion provides additional mass of absorbent material to cater for heavy menses, i.e., large volumes, and in use rests on the pelvic floor musculature and inhibits the body of the tampon from slipping down the vagina.

The trailing end or tail portion of the body may be widened in plan view relative to a leading end or nose portion of the body. This widening may also provide for additional mass of absorbent material.

The body may include absorbent fibres arranged or orientated with one end of the fibres closer to a central longitudinal axis of the body and the other end of the fibres further from the central longitudinal axis of the body. This orientation of the fibres advantageously allows the fibres to wick menses toward a central area of the body, i.e. toward the central longitudinal axis of the body.

The upper surface and the lower surface may converge towards each other to define the side edges and two longitudinally extending, bilaterally projecting wings. The side edges and, hence, the wings may be foldable underneath the body to facilitate insertion of the tampon into a vagina.

The body may include at least one fibre zone populated by fibres which contract, shorten or shrink when in contact with menses thereby actively to unfold or deploy the bilaterally extending wings in situ in a vagina. The at least one fibre zone may be located just beneath, or may define at least a portion of, the upper surface of the body. The body may include two longitudinally and laterally extending fibre zones spaced from each other by a longitudinally extending central portion of the upper surface of the body. As hereinbefore mentioned, the side edges of the body may thus be folded underneath the rest of the body, thereby bending or folding the wings, to facilitate insertion of the tampon in a vagina. Once the tampon, or at least the fibre zones have in use been wetted, the fibres of the fibre zones shrink to pull the sides edges out from underneath the body so that the wings project laterally in opposite directions, filling the vagina. Thus, the fibre zones advantageously provide means for actively deploying or unfolding a tampon in situ in a vagina.

Instead of or in addition to the zones of fibres which contract, shorten or shrink when in contact with menses, the tampon may include a biased template inside the body of the tampon and/or elastic fibres which are woven into the body of the tampon to assist with or effect active unfolding or deployment of the wings in situ in a vagina.

The tampon may further include a plurality of surface formations in the form of strips or bands extending over the bilaterally extending wings so that portions of the strips or bands are under tension and portions thereof are under compression when the side edges of the body are folded underneath the body, thereby to assist with or effect active unfolding or deployment of the wings in situ in a vagina.

The tampon may be a tampon which includes at least one surface formation in accordance with the first aspect of the invention.

In accordance with a third aspect of the invention, there is provided a tampon which includes an elongate absorbent body, a portion of an external surface of the absorbent body being coated by a coating.

The tampon may be a tampon in accordance with the second aspect of the invention.

In accordance with a fourth aspect of the invention, there is provided a tampon which has a particular correct angular orientation relative to its longitudinal axis, with which it is to be inserted into a vagina, the correct angular orientation being clearly visible to a user.

The correct angular orientation may be marked on the tampon or on packaging in which the tampon is supplied.

Thus, when the tampon is inserted correctly in its specific orientation, the wings, when unfolded, project laterally in opposite directions, filling the vagina. This is in contrast with the typical circular cylindrical tampons of the prior art, which can be inserted into a vagina in any angular orientation relative to its longitudinal axis and which are not provided with any indications regarding orientation. Some of the circular cylindrical tampons of the prior art have longitudinally extending seams caused by folding and compressing a rectangular absorbent body into a cylindrical shape. When such a prior art tampon becomes moist, the seam may widen as the absorbent body swells, effectively changing the shape of the absorbent body from being circular cylindrical to being more oval or flattened. This does not present a problem when the seam is located on top of the tampon or underneath the tampon when the tampon is inserted into a vagina. However, when the seam is located along one of the sides of the tampon, the change in shape of the absorbent body is undesirable and actually leads to leakage of menstrual fluid.

The body of the tampon may have a length of between 2 cm and 8 cm, e.g. 5 cm. The body may have a width of between 1 cm and 4 cm, e.g. 2 cm. The body may have a thickness of between 0.2 cm and 2 cm, e.g. 0.5 cm.

The invention will now be described, by way of example, with reference to the accompanying diagrammatic drawings, in which.

Referring to FIGS. 1 to 4 of the drawings, reference numeral 10 generally indicates a catamenial tampon in accordance with the invention. The tampon 10 comprises an elongate body 12 of an absorbent material. The body 12 has a leading end or nose 14 and a longitudinally opposed trailing end or tail 16.

Figure 4:
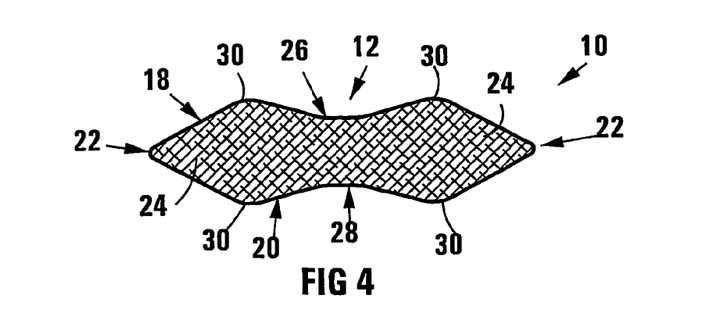
FIG. 4 shows a cross-sectional view of the tampon of FIG. 1, taken at IV-IV in FIG. 2.

The body 12 is non-circular in outline in end view and in cross-section, as can best be seen in FIG. 4, with extremities of the body 12 falling on the outline of an oval or ellipse in end view. The body 12 has a width which is greater than a thickness thereof, as well as a length that is greater than its width. Typically, the body 12 has a length of about 5 cm, a width of about 2 cm, and a maximum thickness of about 0.75 cm.

The body 12 defines an upper or superior surface 18, a lower or posterior surface 20, and two opposed side edges 22 which extend longitudinally. The upper surface 18 and the lower surface 20 converge towards each other to define the side edges 22 and also to define two longitudinally extending bi-laterally projecting wings 24. The side edges 22 are somewhat rounded as can be seen in FIG. 4.

Both the upper surface 18 and the lower surface 20, in central longitudinally extending portions thereof, are non-planar, being concave when the body 12 is viewed in cross-section or end view (FIG. 4). The central longitudinally extending concave portion of the upper surface 18 is indicated by reference numeral 26, and the central longitudinally extending concave portion of the lower surface 20 is indicated by reference numeral 28. Between the central longitudinally extending portions 26, 28, and the wings 24, a pair of laterally spaced upper, as well as a pair of laterally spaced lower, ridges or shoulders 30 which extend for the length of the body 12, are defined.

The body 12 comprises absorbent elongate fibres arranged or orientated at right angles relative to a central longitudinal axis (not shown) of the body 12. In other words, each fibre is arranged side-ways or radially, having one end closer to the central longitudinal axis of the body 12 and the other end further from the central longitudinal axis of the body 12.

The upper surface 18 of the body 12 converges gradually towards the lower surface 20 over a major portion of the length of the body 12, and then converges or drops down more sharply and in a slightly concave fashion (in side view) towards the lower surface 20 to end in the leading end or nose 14, which is wedge-shaped and has a rounded leading edge. This configuration is clearly shown in FIG. 3 of the drawings. In another embodiment of the invention (not shown) the upper surface 18 and the lower surface 20 are parallel to each other, except for the leading end 14.

Figure 1:
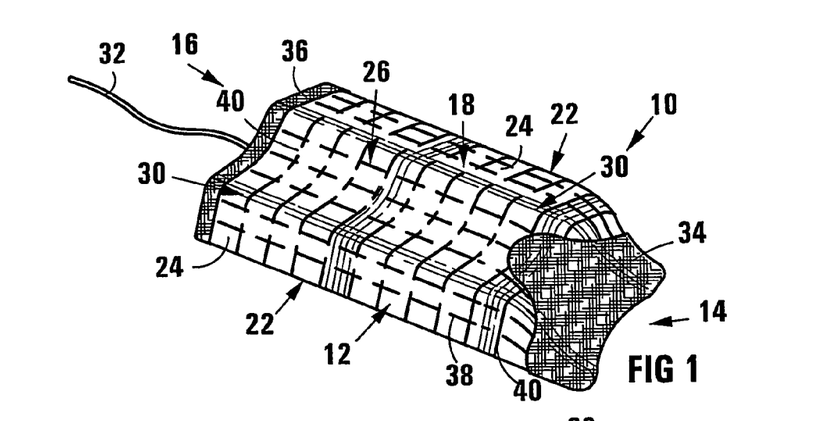
FIG. 1 shows a three dimensional view of one embodiment of a tampon in accordance with the invention.
Figure 2:
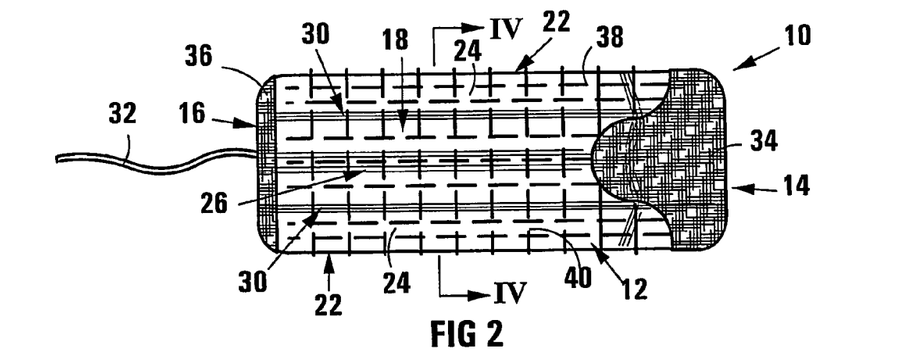
FIG. 2 shows a top plan view of the tampon of FIG. 1.
Figure 3:
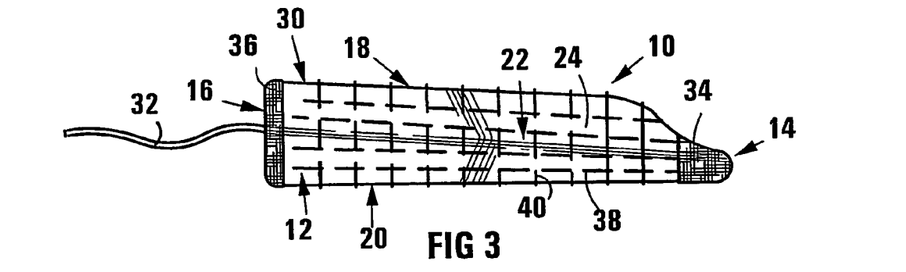
FIG. 3 shows a side view of the tampon of FIG. 1.

Corners of the body 12 are rounded, as is clearly shown in FIG. 2 of the drawings. A string 32 is attached to the body 12, to the trailing end or tail 16 thereof.

The tampon 10 includes surface formations of a thermoplastic, elastomeric or resin material which cover portions of the upper surface 18 and the lower surface 20 of the body 12. A leading end or nose portion of the body 12 and an area immediately behind the leading end or nose portion, and extending rearwardly onto the central longitudinally extending concave portion 26, is coated with a coating 34 of said material.

A trailing end or tail portion of the body 12 is coated by a coating 36 of said material. The coating 36 defines an end cap which covers the trailing or tail end portion 16 of the body 12 and also extends circumferentially around the trailing or tail end portion of the body 12.

Discontinuous elongate strips or bands 38 (not shown in FIG. 4) of said material extend longitudinally over the upper surface 18 and lower surface 20 of the body 12 between the coatings 34, 36. The bands or strips 38 are spaced from each other and are substantially parallel.

A plurality of transversely arranged bands or strips 40 of said material intersect at least some of the longitudinally extending bands or strips 38. The transversely arranged bands or strips 40 are longitudinally spaced from each other and extend completely around the body 12. The bands 40 are continuous in those areas of the body 12 of the tampon 10 which are intended to be constricted, and discontinuous in areas where constriction is not desired, to allow for expansion of the body 12 of the tampon 10.

The tampon 10 is used in similar fashion to a conventional tampon. However, unlike a conventional circular cylindrical tampon, the concave central longitudinally extending portions 26, 28 of the upper and lower surfaces 18, 20, conform in use with the anterior wall of the vagina, which is convex as a result of pressure from the bladder, and with the posterior wall of the vagina, which is convex as a result of the presence of the rectum, respectively. This enhances comfort and reduces leakage of fluid and may aid in preventing slippage of the tampon 10. The two wings 24 fill the lateral extremities of the vagina, thus further inhibiting leakage of menstrual fluid past the tampon 10. The longitudinally extending shoulders or ridges 30 provide areas of resistance inhibiting the tampon 10 from slipping out of the vagina. Furthermore, the thickened portions of the body 12, defined between the ridges 30 on the upper surface 18 and the ridges 30 on the lower surface 20 of the body 12, provides additional mass of absorbent material, providing the tampon 10 with a higher fluid absorbing capacity. The orientation of the absorbent fibres advantageously allows the fibres to wick menstrual fluid toward the central longitudinal axis of the body.

The coating 34 over the nose of the body 12 renders the tampon easier and less painful to insert and it allows the leading end or nose easily to slip into the posterior vaginal fornix. As a result, the tampon can be located higher up in the vagina, thereby making use of the extra space provided by the posterior vaginal fornix. Pressure from the cervix of the anteverted uterus may serve to pinch the tampon nose between the cervix and posterior vaginal wall thereby further inhibiting distal slippage of the tampon.

A portion of the coating 34 is in use in contact with the cervix of the user. As is well known to medical practitioners, the delicate lining of the cervical canal (endocervical epithelium) of some women is exposed at the opening of the cervix (external cervical os). That portion of the coating 34 in contact with the cervix, and in particular the cervix opening, may reduce microtrauma to ectropion or erosion caused by friction between the delicate epithelium skin and the absorbent and abrasive fibres of an uncoated tampon. Microtrauma to the epithelium of erosion or ectropion may interrupt the integrity of the epithelium to microorganisms resulting in cervicitis, vaginal discharge and abnormal vaginal bleeding. Protection of the epithelium and the reduction of genital tract microtrauma are very desirable to combat the transmission of HIV.

In use, the coating 34 inhibits expansion or swelling of the leading end or nose portion of the absorbent body 12, due to absorption of menses by the body 12. The nose portion of the body 12 thus in use retains its shape and dimensions substantially. As a result, the risk of plugging of the cervix and resultant retrograde menstruation is reduced by the presence of the coating 34 on the nose portion of the body 12 and the first few circumferential bands or strips 40 around the body 12 in the region behind the coating 34.

As mentioned, the coating 36 defines an end cap for the trailing end or tail portion 16 of the absorbent body 12. The inventor expects the coating 36 to inhibit discharge of menses from the trailing end or tail portion of the absorbent body 12 caused by squeezing of the absorbent body 12 during movement of the body of the user. Furthermore, the coating 36 inhibits expansion or swelling of the tail portion of the body 12, thereby ensuring that the tail portion in use more or less retains its shape and dimension. The formation of a tapered or pointed tail as occurs in the prior art due to swelling is thus inhibited, which reduces the risk that the absorbent body 12 will wedge between the levator ani of the user. This may be of particular importance to those women who regularly suffer discomfort and pain due to the wedging of a conventional tampon between the levator ani.

The discontinuous longitudinally extending bands or strips 38 facilitate insertion of the tampon 10 into a vagina, while allowing longitudinal expansion of the body 12. The bands or strips 38 are raised above the surface of the absorbent body 12 and are easily lubricated by body fluids. Insertion of the tampon 10 into a vagina is thus easier and less microtrauma is caused to the vaginal mucosa of a user during insertion and the tampon will be more comfortable to wear by allowing body movement without microfriction.

The transversely arranged bands or strips 40 define a raised pattern on the exterior surface of the absorbent body 12. The transversely arranged bands or strips 40 in use interact with the rugae of the vagina, thereby assisting in inhibiting slipping of the tampon 10 in use towards the vaginal opening. They also function to inhibit expansion of the tampon in areas where constriction is desired.

In order to insert the tampon 10 into a vagina, the wings 24 may be folded such that the side edges 22 are located below the rest of the body 12. The tampon 10 is then inserted by means of an applicator or with a finger. Deployment of the wings 24 in the vagina may then be actively assisted by the transversely arranged bands or strips 40. As will be appreciated, when the side edges 22 are located below the rest of the body 12, the portions of the bands or strips 40 on the upper surface 18 of the body 12 will be stretched, whereas the portions of the bands or strips 40 on the lower surface 20 of the body 12 will be compressed. This stretching and compression of the bands or strips 40 assist in actively deploying the wings 24 in use.

In a variant embodiment of the tampon 10, which is not shown the tampon has a shape and size identical to that of the tampon 10, but does not include any surface formations. Accordingly, the variant embodiment of the tampon is used in a fashion similar to the tampon 10 and, with the exception of the surface formations, functions in similar fashion and poses the same advantages as the tampon 10.

Figure 5:
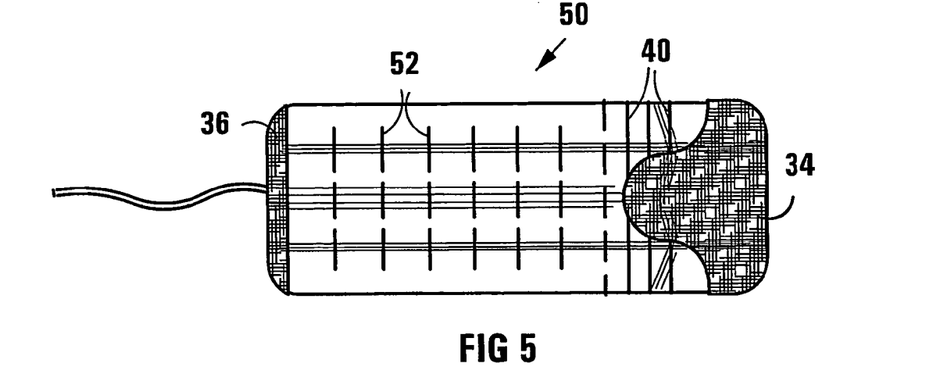
FIG. 5 shows a top plan view of another embodiment of a tampon in accordance with the invention.
Figure 6:
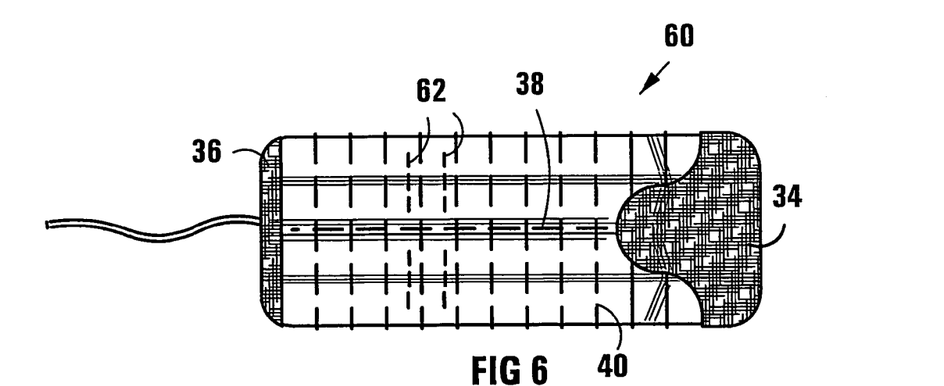
FIG. 6 shows a top plan view of yet another embodiment of a tampon in accordance with the invention.
Figure 7:
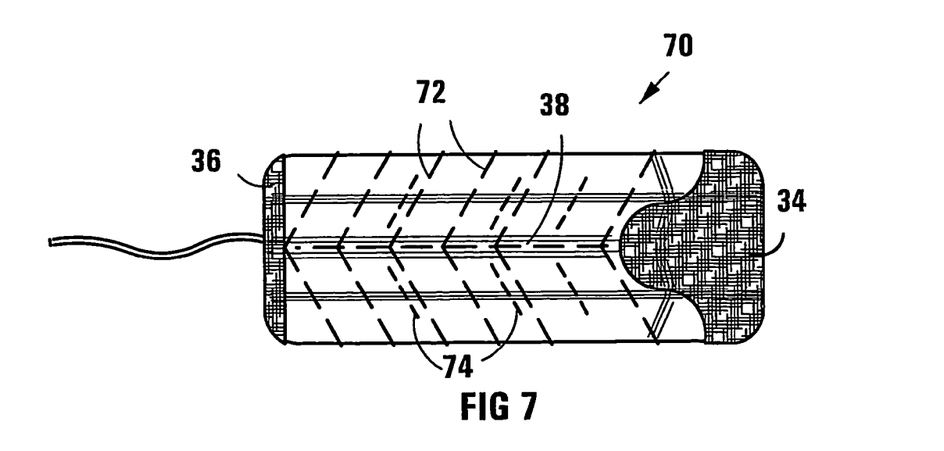
FIG. 7 shows a top plan view of still another embodiment of a tampon in accordance with the invention.

Referring to FIGS. 5, 6 and 7 of the drawings, reference numerals 50, 60 and 70 respectively indicate further embodiments of a tampon in accordance with the invention. The tampons 50, 60, 70 are similar to the tampon 10 and the same reference numerals are thus used to indicate the same or similar parts or features. As can be clearly seen in FIGS. 5, 6 and 7, the tampons 50, 60 and 70 differ from each other and from the tampon 10 in the number and arrangement of the bands or strips 38, 40, if present, and in the presence of other raised surface formations.

In FIG. 5, the tampon 50 includes, in addition to the coatings 34, 36, and three continuous bands or strips 40, a plurality of transversely extending rows of short spaced raised strips 52. With reference to FIG. 6 of the drawings, the tampon 60 includes, in addition to the coatings 34, 36, a single discontinuous longitudinally extending strip 38 and a plurality of transversely arranged strips 40, also a plurality of transversely arranged rows of raised dots 62, only two rows of which are shown. With reference to FIG. 7 of the drawings, the tampon 70 includes the coatings 34, 36, a single longitudinally extending strip 38 and a plurality of V-shaped surface formations 72. Surface formations in the form of raised dots 74 arranged in a V are also provided.

The tampons 50, 60, 70 are used in the same fashion as the tampon 10, with the formations 52, 62, 72, 74 assisting in retaining the tampon in the desired location in the vagina.

Figure 8:
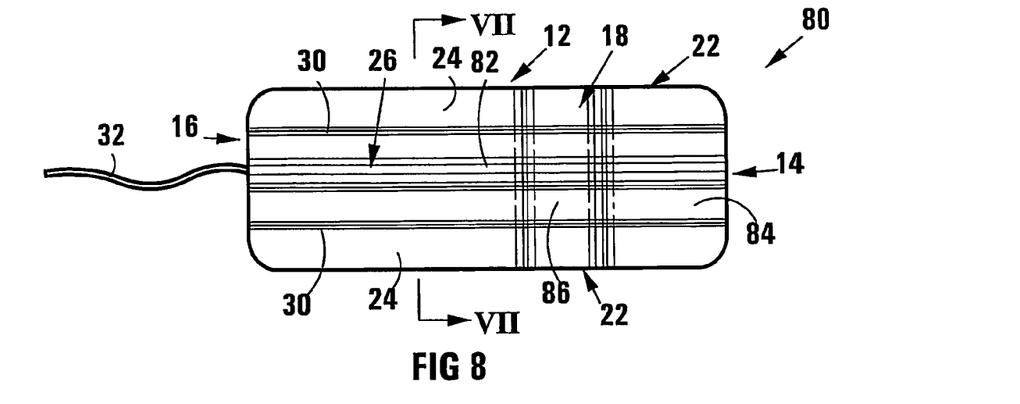
FIG. 8 shows a top plan view of a further embodiment of a tampon in accordance with the invention.
Figure 9:
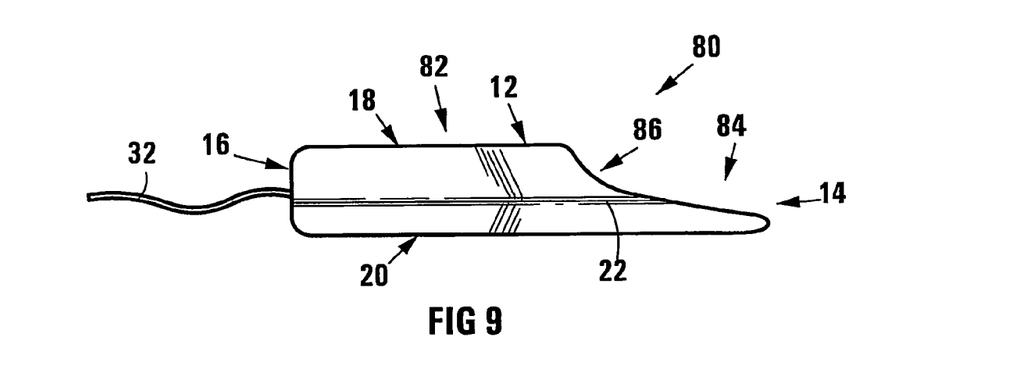
FIG. 9 shows a side view of the tampon of FIG. 8.
Figure 10:
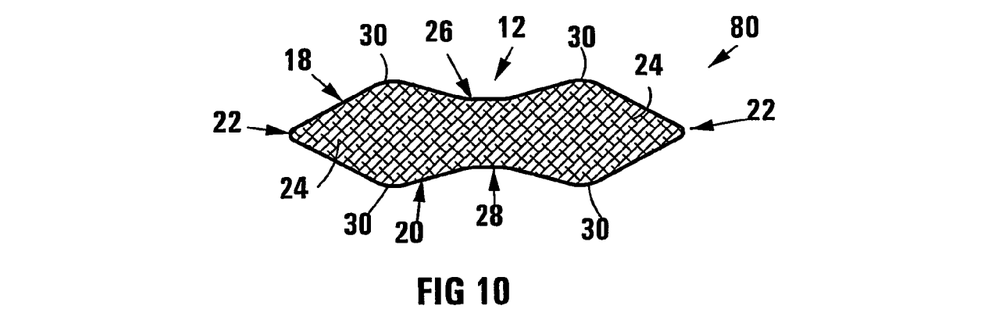
FIG. 10 shows a cross-sectional view of the tampon of FIG. 8, taken at X-X in FIG. 8.

Referring now to FIGS. 8 to 10 of the drawings, reference numeral 80 generally indicates another embodiment of a catamenial tampon in accordance with the invention. The tampon 80 is similar to the tampons 10, 50, 60, 70 and unless otherwise indicated, the same reference numerals used in relation to the tampons 10, 50, 60, 70 are used to indicate the same or similar parts or features of the tampon 80. The tampon 80 does not have any surface formations.

The tampon 80 also has a length of about 5 cm and a width of about 2 cm. However, unlike the tampon 10, a 3 cm long distal portion 82 of the body 12 of the tampon 80 is thickened compared to a 2 cm long leading portion 84 of the body 12. The distal portion 82 has a thickness of about 1.5 cm whereas the leading portion 84 has a thickness of about 0.5 cm. A transitional region 86 between the distal portion 82 and the front or leading portion 84 is concavely curved.

The thickened distal portion 82 provides an additional mass of absorbent material to cater for larger volumes of menstrual fluid than can be accommodated by the tampon 10. In use, the distal portion 82 rests on the pelvic floor musculature and advantageously inhibits the body 12 of the tampon 80 from slipping down the vagina. Advantageously, the concavely curved transitional region 86 accommodates in use the portio vaginalis of the cervix uteri, with the front or leading portion 82 of the body 12 fitting into the posterial vaginal fornix.

Figure 11:
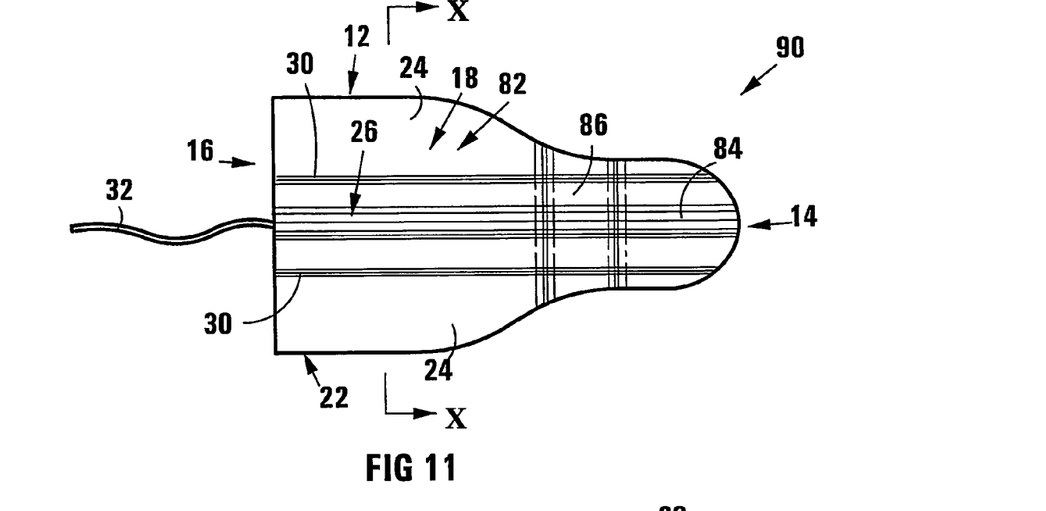
FIG. 11 shows a top plan view of yet a further embodiment of a tampon in accordance with the invention.
Figure 12:
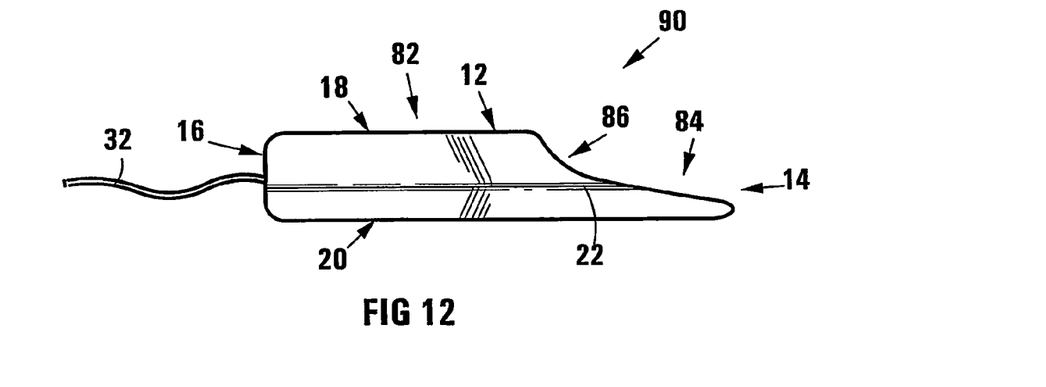
FIG. 12 shows a side view of the tampon of FIG. 11.
Figure 13:
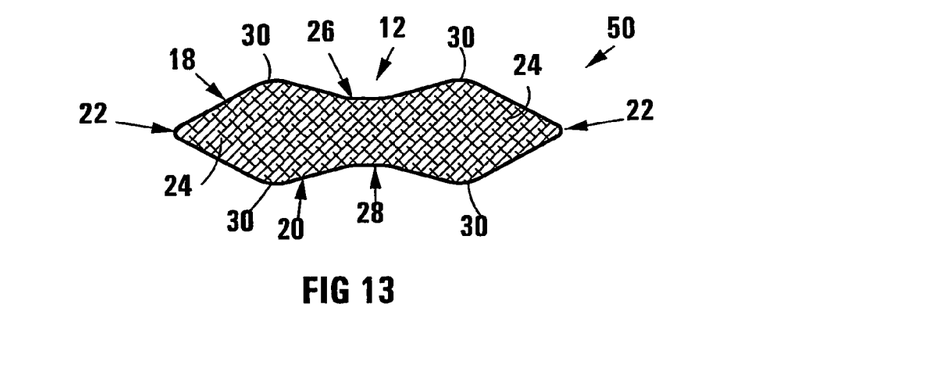
FIG. 13 shows a cross-sectional view of the tampon of FIG. 11, taken at XIII-XIII in FIG. 11.

Referring now to FIGS. 11 to 13 of the drawings, yet another embodiment of a tampon in accordance with the invention is generally indicated by reference numeral 90. Again, the tampon 90 is similar to the tampons 10, 50, 60, 70, 80 and unless otherwise indicated, the same reference numerals used in relation to the tampons 10, 50, 60, 70, 80 are used to indicate the same or similar parts or features of the tampon 90. The tampon 90 does not have any surface formations.

The distal portion 82 of the tampon 90 is also thickened compared to the leading portion 84, similar to the tampon 80. However, in addition, the distal portion 82 is also wider than the leading portion 84. A smooth transition is provided between the distal portion 82 and the leading portion 84, the side edges 22 being gently curved.

The widened distal portion 82 allows the tampon 90 to absorb even more menstrual fluid than the tampon 80. Thus, as will be appreciated, the tampons 10, 50, 60, 70, 80, 90 provide a user with a choice of tampons to be used with light, moderate or heavy menses. In addition, the widened distal portion 82 of the tampon 90 makes it even more difficult for the tampon 90 to slip from the vagina.

Figure 14:
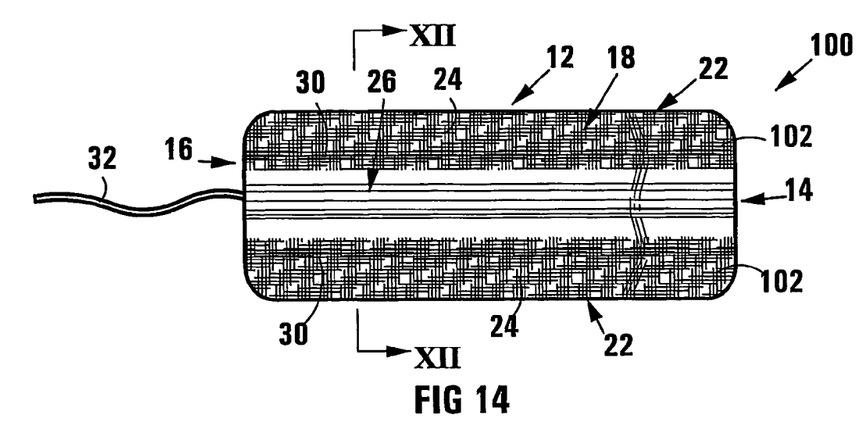
FIG. 14 shows a top plan view of still a further embodiment of a tampon in accordance with the invention.
Figure 15:
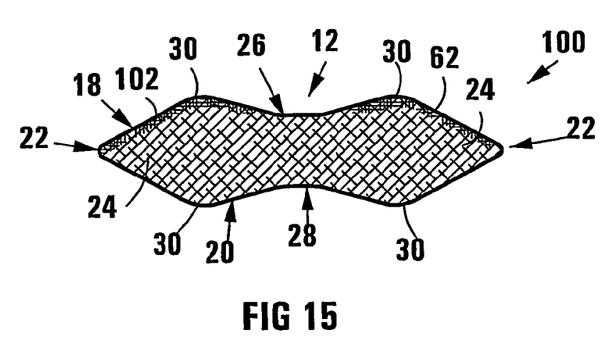
FIG. 15 shows a cross-sectional view of the tampon of FIG. 14, taken at XV-XV in FIG. 14.
Figure 16:
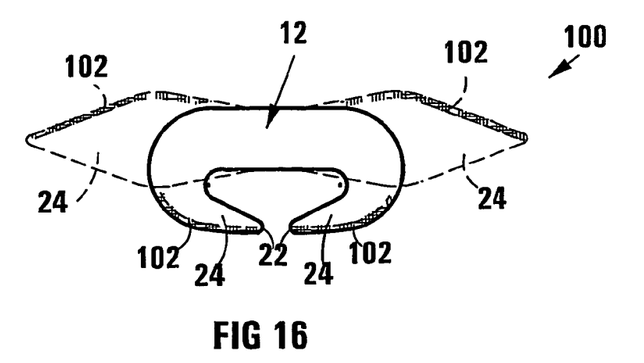
FIG. 16 shows an end view of the tampon of FIG. 14, folded for insertion into a vagina.

A further embodiment of a tampon in accordance with the invention is generally indicated by reference numeral 100 in FIGS. 14 to 16 of the drawings. The tampon 100 is in external appearance identical to the tampons 10, 50, 60, 70 and the same reference numerals are thus used to indicate the same or similar parts or features.

The only difference between the tampon 100 and the tampons 10, 50, 60, 70 is that the tampon 100 includes, instead of the coatings 34, 36 and the bands or strips 38, 40, two fibre zones 102 populated by fibres which contract, shorten or shrink when in contact with menstrual fluid. As can be clearly seen in FIGS. 14 and 15 of the drawings, the fibre zones 102 define portions of the upper surface 18 of the body 12 and are located adjacent the central longitudinally extending concave portion 26 of the upper surface 18. The fibre zones 102 are thus spaced from each other and extend longitudinally as well as laterally.

In order to insert the tampon 100 into a vagina, a method similar to that for inserting any of the aforementioned embodiments is followed, i.e. the wings 24 are folded such that the side edges 22 are located below the rest of the body 12, as shown in FIG. 16 of the drawings. The tampon 100 is then inserted by means of an applicator or with a finger. Once the fibres of the fibre zones 102 become wetted with menstrual fluid, they shorten, thereby unfolding or deploying the wings 24, as shown in broken lines in FIG. 16.

The Applicant believes that the tampons of the invention, as illustrated, can be worn with increased comfort and safety compared to conventional tampons without surface formations configured to inhibit expansion and/or to facilitate insertion and seating of the tampon and/or with a conventional circular cylindrical shape.

The applicant further believes that the tampons of the invention, as illustrated, have, due to their shape and configuration, an improved efficiency in preventing leakage of menses or menstrual fluid.

The invention claimed is:

1. A tampon which includes an elongate absorbent body which is longer than the body is wide and longer than the body is thick with a line along which the length of the body is taken passing through a leading end portion at a first end of the elongate body which has a forward facing surface and through a longitudinally opposed trailing end portion at a second end of the elongate body which has a rearward facing surface, the leading end portion and the trailing end portion of the elongate absorbent body thus being longitudinally spaced with the leading end portion in use leading the trailing end portion during insertion of the tampon in a vagina, at least one of at least a portion of the forward facing surface and at least a portion of the rearward facing surface being coated with a surface formation in a form of a coating of a material with reduced water absorbent properties compared to a material of the absorbent body, the material of the coating having an equilibrium contact angle of water on a smooth surface of the material of the coating of between 30° and 120° and the surface formation in the form of the coating inhibiting in use expansion of at least a portion of the absorbent body coated by the surface formation in the form of the coating due to absorption of menses by the absorbent body, at least a portion of the absorbent body between the forward facing surface and the rearward facing surface not being constricted by said surface formation in the form of the coating to allow for expansion of said portion of the absorbent body in use due to absorption of menses by the absorbent body, further comprising at least one of at least one surface formation and a portion of the at least one surface formation, which is in a form of one of a thin band and a strip applied to the longitudinally extending exterior surface of the absorbent body between the leading end portion and the longitudinally opposed trailing end portion.

2. The tampon as claimed in claim 1, in which the surface formation in the form of the coating is selected from the group consisting of synthetic plastics material with the equilibrium contact angle of water on the smooth surface of the material of between 30° and 120° and a polymeric material with the equilibrium contact angle of water on the smooth surface of the material of between 30° and 120°.

3. The tampon as claimed in claim 1, in which an exterior surface portion of the tampon which in use will be in contact with the cervix of a user includes said surface formation in the form of a coating.

4. The tampon as claimed in claim 1, which includes the surface formation in the form of said coating on at least a portion of the rearward facing surface and in which said coating inhibits in use expansion of the trailing end portion of the absorbent body.

5. The tampon as claimed in claim 4, in which the surface formation in the form of the coating defines an end cap for the trailing end portion of the absorbent body.

6. The tampon as claimed in claim 1, in which a plurality of one of the bands and strips are provided on the exterior surface of the absorbent body, and in which at least some of the one of bands and strips are in the form of one of broken and discontinuous lines which between adjacent such lines define uncoated areas.

7. The tampon as claimed in claim 6, in which some of the one of bands and strips longitudinally extend over the exterior surface of the absorbent body and are transversely spaced from each other, and in which some of the one of bands and strips transversely extend over the exterior surface of the absorbent body and are longitudinally spaced from each other.

8. The tampon as claimed in claim 1, in which at least one surface formation in the form of the coating is of an elastic material.

9. The tampon as claimed in claim 1, in which at least one of the surface formation and a plurality of surface formations in the form of the coating stand proud of the exterior surface of the absorbent body thereby to one of form and define a raised formation on the exterior surface of the absorbent body.

10. A tampon which includes an elongate absorbent body which is non-circular in outline in an end view, a width of the body being greater than a thickness thereof and a length of the body being greater than the width of the body, the length being taken in a direction of said end view, the width being taken in a direction perpendicular to said direction of the end view and the thickness being taken in a direction perpendicular to said direction of the end view and perpendicular to said direction of the width, the tampon having a particular correct angular orientation relative to said direction of the end view with which the tampon is to be inserted into a vagina, the correct angular orientation being clearly visible to a user, wherein the body defines an upper or superior surface, an opposed lower or posterior surface, and two opposed side edges which extend longitudinally, the width of the body thus being taken between the opposed side edges and the thickness of the body being taken between the upper surface and the lower surface, at least one of the upper surface and the lower surface being concave when a cross-section transverse to the direction of the end view is viewed in said direction of the end view, providing the body with a longitudinally extending depression which is concave when said cross section is viewed in said direction of the end view, further wherein the upper surface and the opposed lower surface converge towards each other to define the side edges and two longitudinal extending, bilaterally projecting wings, the side edges and, hence, the wings being folded underneath the body to facilitate insertion of the tampon into the vagina, wherein said tampon further comprises a plurality of surface formations in the form of one of strips and bands extending over the bilaterally extending folded wings so that portions of the one of strips and bands are under a tension and portions thereof are under a compression, thereby to assist with or effect an active unfolding or a deployment of the folded wings in situ in the vagina.

11. The tampon as claimed in claim 10, in which both of at least a portion of the upper surface and at least a portion of the lower surface are concave when said cross-section transverse to said direction of the end view is viewed in said direction of the end view, providing the body with opposed longitudinally extending depressions which are concave when said cross-section is viewed in said direction of the end view, the concave depression in the upper surface in use conforming to the shape of an anterior wall of a vagina which is convex as a result of bladder pressure and the concave depression in the lower surface in use conforming to the shape of a posterior surface of a vagina which is convex as a result of the presence of a rectum.

12. The tampon as claimed in claim 10, in which the upper surface of the body converges or drops down towards the lower surface of the body to end in a rounded leading end or nose of reduced thickness when the body is viewed in side view in said direction in which the width of the body is taken and in which corners of the body are rounded when the body is viewed in plan view in said direction in which the thickness of the body is taken.

13. The tampon as claimed in claim 10, in which the body is generally rectangular in plan view when viewed in the direction in which the thickness of the body is taken and in which the body is thicker in a trailing end portion thereof than in a longitudinally opposed leading end portion thereof, where these thicknesses are taken in a common plane transverse to the direction in which the width of the body is taken.

14. The tampon as claimed in claim 13, in which a transitional region between the trailing end portion and the longitudinally opposed leading end portion is concavely curved when the body is viewed in side view in the direction in which the width of the body is taken and in which the trailing end portion of the body is wider than the longitudinally opposed leading end portion of the body, where these widths are taken in a common plane transverse to the direction in which the thickness of the body is taken.

15. The tampon as claimed in claim 10, which includes at least one of a template inside the body of the tampon and elastic fibres which are woven into the body of the tampon in use to one of assist with and effect one of active unfolding and deployment of the folded wings in situ in a vagina.

16. The tampon as claimed in claim 10, which includes at least one surface formation in the form of a coating, said surface formation in the form of a coating being formed of a material different to the absorbent body, applied over an exterior surface of the absorbent body, the surface formation in the form of a coating in use inhibiting expansion of at least one of a leading end portion and a longitudinally opposed trailing end portion of the absorbent body in use due to absorption of menses by the absorbent body, where said leading end portion and said trailing end portion are longitudinally spaced in the direction in which the length of the absorbent body is taken, at least a portion of the absorbent body between the leading end portion and the longitudinally opposed trailing end portion not being constricted by said surface formation in the form of a coating to allow for expansion of said portion of the absorbent body in use due to absorption of menses by the absorbent body.

17. The tampon as claimed in claim 1, in which the absorbent body is non-circular in outline in end view, the width of the body being greater than the thickness thereof, and the length of the body being greater than the width of the body, the length being taken in the direction of said end view, the width being taken in a direction perpendicular to said direction of the end view and the thickness being taken in a direction perpendicular to said direction of the end view and perpendicular to said direction of the width, the tampon having a particular correct angular orientation relative to said direction of the end view with which the tampon is to be inserted into a vagina, the correct angular orientation being clearly visible to a user.

18. The tampon as claimed in claim 16, in which said surface formation in the form of a coating is comprised of a material with reduced water absorbent properties compared to a material of the absorbent body, the material of the coating having an equilibrium contact angle of water on a smooth surface of the material of the coating of between 30° and 120°.

19. A tampon which includes an elongate absorbent body which is longer than the body is wide and longer than the body is thick with a line along which the length of the body is taken passing through a leading end portion at a first end of the elongate body which has a forward facing surface and through a longitudinally opposed trailing end portion at a second end of the elongate body which has a rearward facing surface, the leading end portion and the trailing end portion of the elongate absorbent body thus being longitudinally spaced with the leading end portion in use leading the trailing end portion during insertion of the tampon in a vagina, at least one of at least a portion of the forward facing surface and at least a portion of the rearward facing surface being coated with a surface formation in the form of a coating of a material with reduced water absorbent properties compared to a material of the absorbent body, the surface formation inhibiting in use expansion of at least a portion of the absorbent body coated by the surface formation due to absorption of menses by the absorbent body, at least a portion of the absorbent body between the forward facing surface and the rearward facing surface not being constricted by said surface formation to allow for expansion of said portion of the absorbent body in use due to absorption of menses by the absorbent body, further comprising at least one of at least one surface formation and a portion of at least one surface formation, which is in a form of one of a thin band and a strip applied to the longitudinally extending exterior surface of the absorbent body between the leading end portion and the longitudinally opposed trailing end portion.

20. The tampon as claimed in claim 10, in which the elongate absorbent body is non-cylindrical.

* * * * *